(12) United States Patent
Notter

(10) Patent No.: US 9,232,914 B2
(45) Date of Patent: Jan. 12, 2016

(54) INDWELLING TRANSFUSION CATHETER, TRANSFUSION CANNULA KIT AND METHOD FOR TESTING A TRANSFUSION SYSTEM

(75) Inventor: Michael Notter, Berlin (DE)

(73) Assignee: CHARITE—UNIVERSITATSMEDIZIN BERLIN (DE)

( * ) Notice: Subject to any disclaimer, the term of this patent is extended or adjusted under 35 U.S.C. 154(b) by 160 days.

(21) Appl. No.: 13/264,195

(22) PCT Filed: Apr. 27, 2010

(86) PCT No.: PCT/DE2010/000479
§ 371 (c)(1),
(2), (4) Date: Dec. 27, 2011

(87) PCT Pub. No.: WO2010/124677
PCT Pub. Date: Nov. 4, 2010

(65) Prior Publication Data
US 2012/0091196 A1 Apr. 19, 2012

(30) Foreign Application Priority Data
Apr. 28, 2009 (DE) .......................... 10 2009 018 837

(51) Int. Cl.
*A61B 5/15* (2006.01)
*A61M 25/00* (2006.01)
(Continued)

(52) U.S. Cl.
CPC .......... *A61B 5/1405* (2013.01); *A61M 25/0017* (2013.01); *A61J 2205/30* (2013.01); *A61J 2205/60* (2013.01); *A61M 1/0209* (2013.01);
(Continued)

(58) Field of Classification Search
CPC ......... G06Q 50/22; A61M 2025/0008; A61M 2205/60; A61M 2205/6072; A61M 2205/6054; A61M 2205/6063; A61M 1/02; G06F 19/322; G06F 19/323
USPC ................................... 235/487, 492; 604/411
See application file for complete search history.

(56) References Cited

U.S. PATENT DOCUMENTS 3,619,568 A * 11/1971 Taplin ........................... 235/449
4,122,947 A 10/1978 Falia ............................. 206/569
(Continued)

FOREIGN PATENT DOCUMENTS

DE 102004055989 A1 5/2006
EP 1346740 A2 9/2003
(Continued)

OTHER PUBLICATIONS

English Translation of Notter DE 1020040550989.*
(Continued)

*Primary Examiner* — Christopher Stanford
(74) *Attorney, Agent, or Firm* — Ostrolenk Faber LLP

(57) ABSTRACT

The present disclosure relates to an indwelling catheter having a cannula device (2, 4) and a reservoir, which is connected in a use position to the cannula device (2, 4), such that blood can flow from the cannula device (2, 4) into the reservoir (6), wherein the housing (3) has housing identifiers (8) and the reservoir (6) has reservoir identifiers (9), and the housing identifiers (8) and the reservoir identifiers (9) give mutually assigned codes. In addition, the disclosure relates to a transfusion cannula kit and the method for testing a transfusion system.

2 Claims, 2 Drawing Sheets

Figure 1:
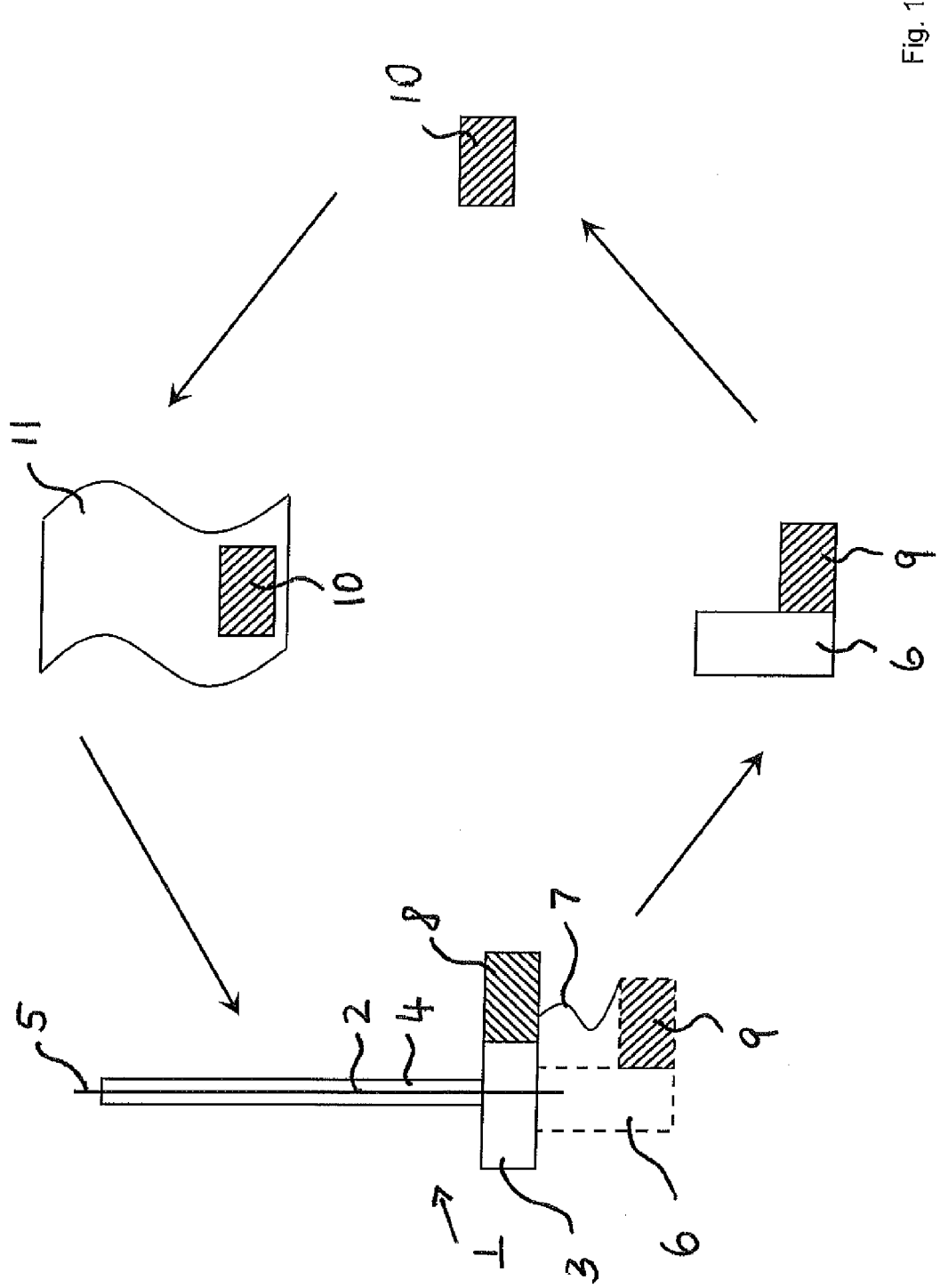

(51) Int. Cl.
  *G06Q 50/24* (2012.01)
  *G06F 19/00* (2011.01)
  *A61M 1/02* (2006.01)
  *G06Q 50/22* (2012.01)

(52) U.S. Cl.
  CPC .... *A61M 2025/0008* (2013.01); *A61M 2205/60* (2013.01); *A61M 2205/6063* (2013.01); *A61M 2205/6072* (2013.01); *G06F 19/366* (2013.01); *G06Q 50/22* (2013.01); *G06Q 50/24* (2013.01)

(56) References Cited

U.S. PATENT DOCUMENTS

| | | | | |
|---|---|---|---|---|
| 4,349,035 | A * | 9/1982 | Thomas et al. | 600/579 |
| 5,125,920 | A * | 6/1992 | Ishida | 604/410 |
| 5,640,000 | A * | 6/1997 | Spriet et al. | 235/375 |
| 5,971,972 | A * | 10/1999 | Rosenbaum | 604/411 |
| 6,402,702 | B1 * | 6/2002 | Gilcher et al. | 600/573 |
| 2004/0182734 | A1 * | 9/2004 | Demay et al. | 206/459.1 |
| 2004/0193453 | A1 | 9/2004 | Butterfield et al. | |
| 2005/0086071 | A1 * | 4/2005 | Fox et al. | 705/2 |
| 2009/0291449 | A1 * | 11/2009 | Knapp et al. | 435/6 |
| 2010/0137744 | A1 | 6/2010 | Notter | |

FOREIGN PATENT DOCUMENTS

| | | |
|---|---|---|
| EP | 1850289 A1 | 1/2005 |
| WO | WO 03/026724 A1 | 4/2003 |
| WO | WO 2006/053516 A1 | 11/2004 |
| WO | WO 2007/128144 A1 | 11/2007 |
| WO | WO 2008/114164 A1 | 9/2008 |

OTHER PUBLICATIONS

International Search Report dated Oct. 5, 2010, issued in corresponding international application No. PCT/DE2010/000479.

Notification of Transmittal of Translation of the International Preliminary Report on Patentability and Written Opinion of the International Searching Authority dated Nov. 24, 2011 issued in corresponding PCT International Application No. PCT/DE2010/000479 (Total 9 pages).

European Office Action, dated Mar. 12, 2015, issued in corresponding European Patent Application No. EP 10 722 559.1. Total 4 pages.

* cited by examiner

INDWELLING TRANSFUSION CATHETER, TRANSFUSION CANNULA KIT AND METHOD FOR TESTING A TRANSFUSION SYSTEM

CROSS REFERENCE TO RELATED APPLICATIONS

The present application is a 35 U.S.C. §371 National Phase conversion of PCT/DE2010/000479, filed Apr. 27, 2010, which claims benefit of German Application No. 10 2009 018 837.1, filed Apr. 28, 2009, the disclosure of which is incorporated herein by reference. The PCT International Application was published in the German language.

The invention relates to an indwelling transfusion catheter, a transfusion cannula kit and a method for testing a transfusion system.

BACKGROUND OF THE INVENTION

Indwelling catheters may be used in the context of a transfusion to be administered to a patient; they may be used in conjunction with a transfusion to be administered to a patient. Other terms include the term peripheral venous catheter. Known indwelling catheters such as those described in the document WO 2006/053516 A1 usually have a puncture cannula consisting of a metal material, such as a steel alloy, for example, and a tip for performing the puncture. When the indwelling catheter is placed in a use position, the puncture cannula is inserted into an indwelling cannula, so that the tip of the puncture cannula protrudes at the front. With the help of the tip of the puncture cannula, the indwelling catheter is positioned by advancing the puncture cannula to the desired blood vessel, in particular into a vein. After positioning the indwelling catheter, the puncture cannula can be removed. The indwelling cannula through which a transfusion fluid can then be injected intravenously remains connected to the blood vessel. On the other hand, it is often impossible to withdraw additional blood through an indwelling catheter that has been put in position because the blood tests performed on such blood samples may be falsified by blood constituents or dilution effects occurring with the ongoing infusions.

It is therefore provided that a blood sample for testing the blood of the patient is to be performed in conjunction with placement of the indwelling catheter. To do so, the indwelling catheter has a reservoir which is connected to the end of the puncture cannula in the use position, so that blood can flow through the puncture cannula into the reservoir. The blood sample removed in this way can be utilized to determine the patient's blood. By means of statistical surveys, it has been ascertained that mistakes with blood products occur with an incidence of approximately 1:10,000 to 1:20,000. Mistakes in obtaining a pre-transfusion blood sample occur in 1:3000 cases.

In conjunction with blood transfusions, it has been proposed that to avoid mistakes in treatment, an armband holding a so-called RFID chip should be placed on the patient. RFID is a technology which is well-known as such and in which electronic memory chips are used to store information. Memory chips that can only be read out or that can additionally be written are known. Data transfer between the memory chips and a read/write device takes place by wireless data communication. A second RFID chip should then be placed on a unit of blood. When a blood transfusion is intended, the electronic information on the armband and that on the unit of blood should both be evaluated electronically using a reader device. In this way, the person responsible for the transfusion can check on whether the blood unit made available is acceptable and suitable for the patient with the armband. In addition, it has been proposed that information about the temperatures at which the blood unit has been stored should be kept on the RFID chip of the blood unit. The RFID chip has a temperature sensor for this purpose.

Use of RFID technology as such as part of the working procedures of a blood bank is known from the document EP 1 850 289 A1.

In daily practice, there have been problems in that armbands on patients have been inadvertently severed and thereby lost. Such situations occur in particular in conjunction with emergency circumstances in which patients must receive care quickly and which are often characterized by complicated situations.

SUMMARY OF THE INVENTION

The object of the invention is to provide improved techniques in conjunction with indwelling catheters, such that safety will be optimized in conjunction with the use of such catheters. In particular this should prevent mistakes in transfusions.

This object is achieved according to the invention by an indwelling catheter, a transfusion cannula kit and a method for testing a transfusion system.

According to one aspect, the invention comprises the idea of an indwelling catheter with a cannula device and a reservoir which is connected to the cannula device in a use position so that blood from the cannula device can flow into the reservoir, where the housing has housing identifiers and the reservoir has reservoir identifiers, and the housing identifiers as well as the reservoir identifiers have codes assigned to one another.

According to another aspect of the invention a transfusion cannula kit with an indwelling catheter having the following features is created: a cannula device and a reservoir which is connected in a use position to the cannula device, such that blood from the cannula device can flow into the reservoir. In addition, identifiers comprising housing identifiers and reservoir identifiers are provided, such that the housing identifiers and the reservoir identifiers have codes assigned to one another.

Another aspect of the invention relates to a method for testing a transfusion system, wherein the method comprises the following steps: providing an indwelling catheter with which a housing is provided with housing identifiers, providing a transfusion liquid in a liquid reservoir which is provided with liquid identifiers, evaluating a code provided by the housing identifiers and a code provided by the liquid identifiers with the help of an evaluation device, in that the two codes are detected and compared, and signals are output by means of the evaluation device as a function of whether or not the codes are recognized as being assigned to one another when compared. In this way, a method for process control in a transfusion is created.

With the proposed indwelling catheter, both the housing with the cannula device formed on it and the reservoir with the assigned identifiers are provided. If the reservoir is filled with blood when the indwelling catheter is positioned and the blood flows through the cannula device into the reservoir, then the blood thereby withdrawn (which is a pre-transfusion blood sample) can be utilized in the reservoir provided with the reservoir identifiers in order to perform a blood test. The reservoir identifiers can identify the blood sample thus taken as belonging to the indwelling catheter, namely the housing with the cannula device, which ultimately corresponds to an assignment of the blood sample to the patient with the indwelling catheter. A code derived from the reservoir identifiers can then be utilized to generate a new identifier and to use it to characterize a transfusion fluid, for example a blood unit using fluid identifiers for example by attaching the new identifier to a transfusion bag by gluing for example. In this way the transfusion fluid is more or less assigned to the housing of the indwelling catheter and thus to the patient having the indwelling catheter. The reservoir identifiers may then be reproduced, for example, or a code derived from the code from the reservoir identifiers may be assigned.

If the transfusion fluid characterized in this way is then to be injected later, the person responsible for this may evaluate the code on the transfusion fluid with the help of a suitable evaluation unit on the one hand and the housing identifiers on the housing of the indwelling catheter may be evaluated and compared on the other hand to thereby ascertain whether the transfusion fluid can be used for the patient for whom the blood is intended and in whom the indwelling catheter can been placed. The evaluation unit is configured to read out the respective code according to the type of identifier used and to compare them. It is then possible to provide for the user of the evaluation unit to receive an optical and/or acoustic signal, for example in the form of different color signals to display the correspondence or non-correspondence of the two codes, as a function of the result of the comparison of the code of the housing identifier on the one hand and the fluid identifier on the other hand.

With the help of the indwelling catheter proposed here, it is possible to consider the process of determination of a blood sample taken from the time of placement of the indwelling catheter in the patient, in particular as part of emergency care or regular transfusion care, until a transfusion through the indwelling catheter, as a closed circuit, in which a code is always retained in the individual steps, said code originating from the indwelling catheter originally inserted and being assigned unambiguously to the patient in whom the indwelling catheter has been inserted.

The codes made available by the different identifiers, i.e., for example, the housing identifiers and the reservoir identifiers may be identical for example in the form of a uniform numerical code. However, it is also possible to provide that the different codes have a shared parent code and contain different identification codes so that it is discernible for example on the basis of the identifying code whether the code belongs to the housing or the reservoir. It is important that the codes can be assigned to a common origin, namely the indwelling catheter that has been put in position.

A preferred further embodiment of the invention provides that the housing identifiers and/or the reservoir identifiers comprise an electronic memory medium that can be read out. The electronically readable memory medium may be in particular an RFID chip. In one embodiment, this may also be designed to be read/writable. Evaluation units, which are configured to read out and/or write to RFID chips, are known as such in various embodiments.

In an expedient embodiment of the invention, it may be provided that the housing identifiers and/or the reservoir identifiers comprise a barcode. Barcode scanners that can be used as such to evaluate barcode markings have been known as such in various specific designs.

According to an advantageous embodiment of the invention, the housing identifiers and/or the reservoir identifiers comprise an alphanumeric code. The alphanumeric code may comprise any number of alphanumeric characters indicating mutually allocated codes.

A refinement of the invention preferably provides that the reservoir is held on the housing with the help of a flexible fastening device. In one embodiment the flexible fastening device is a flexible plastic strip, with which the reservoir is held on the housing of the indwelling catheter. In one embodiment, an intended breaking line may be provided in the area of the flexible fastening device, facilitating the release of the reservoir from the housing of the indwelling catheter. Alternatively, the reservoir can also be separated from the housing if the user detaches the flexible fastening device. In the various embodiments, the reservoir is held on the housing with the help of the flexible fastening, so that it can be brought into the use position in which the at least partial filling of the reservoir with blood occurs when the indwelling catheter is positioned. On the other hand, however, the reservoir may also be released from this use position and then hangs essentially freely on the housing. In a further embodiment, it may be provided that a receptacle, in particular a plug receptacle into which the reservoir can be inserted after and/or before filling with blood, may be formed on the housing. In a further embodiment, the flexible attachment is also provided with a sufficient length, so that the reservoir can be secured on the patient's skin on the side of the inserted indwelling catheter by means of a patch in order to be released and sent for a blood test, for example, after an emergency patient has been transported from the accident site to the hospital.

In an advantageous embodiment of the invention, it may be provided that the reservoir is formed as a passively filling reservoir. This passively filling reservoir has an opening through which air can escape when the reservoir is being filled with blood so that the blood can flow into the reservoir. The opening is preferably covered with a filter. As an alternative to the passively filling reservoir, in one embodiment an actively filling reservoir may be provided in which the filling occurs with the support of a vacuum formed in the interior of the reservoir.

A further embodiment of the invention may provide that the housing identifiers are detachably attached to the housing and/or the reservoir identifiers are attached to the reservoir. A detachable attachment may be embodied for example by means of an adhesive connection.

According to a preferred further embodiment of the invention, the housing identifiers and/or the reservoir identifiers are arranged on a carrier which is detachably arranged on the housing/reservoir. In one embodiment a fastening means with which the carrier and thus the identifier can be attached to the housing and/or the reservoir is formed on the carrier. For example, the fastening means may be provided with a so-called clip connection.

In an expedient embodiment of the invention, it may be provided that additional identifiers for use are provided on the housing and/or on the reservoir separately from the house/reservoir, also showing the assigned code. In this embodiment, a type of magazine having identifiers, which may be used to provide other objects with a code in the same manner, for example, a transfusion bag, is formed on the housing and/or on the reservoir. In one embodiment, the additional identifiers are embodied in the form of one or more adhesive labels or adhesive chips. It is also possible to provide that a plurality of identifiers are interconnected via an intended breaking for tearing location so that they can be separated by the user piece for piece and used. The additional identifiers preferably have an adhesive surface which makes it possible to adhesively attach the identifiers to a desired object.

A further embodiment of the invention may provide that the cannula device is embodied with a puncture cannula for puncturing and with an indwelling cannula formed on the housing through which the puncture cannula runs in an inserted position. In this embodiment the puncture cannula is used for puncturing when the indwelling catheter is inserted. For this purpose a puncture tip is provided on the puncture cannula. Then blood which is in the reservoir when the latter is in the use position then also flows through the puncture cannula. In the use position the reservoir is in fluid connection with the puncture cannula in that the reservoir is attached to the end piece of the puncture cannula for example by means of a so-called Luer connection. Next the reservoir and puncture cannula may be released, whereupon the indwelling cannula remains in place. Alternatively the cannula device is formed with only a cannula which is configured for puncturing when the catheter is inserted as well as for remaining in the patient's body for a subsequent transfusion.

The embodiments explained in detail above in connection with the indwelling catheter may be provided individually or in any combination accordingly for the transfusion cannula kit and in the method for testing a transfusion system.

DESCRIPTION OF PREFERRED EXEMPLARY EMBODIMENTS OF THE INVENTION

Figure 2:
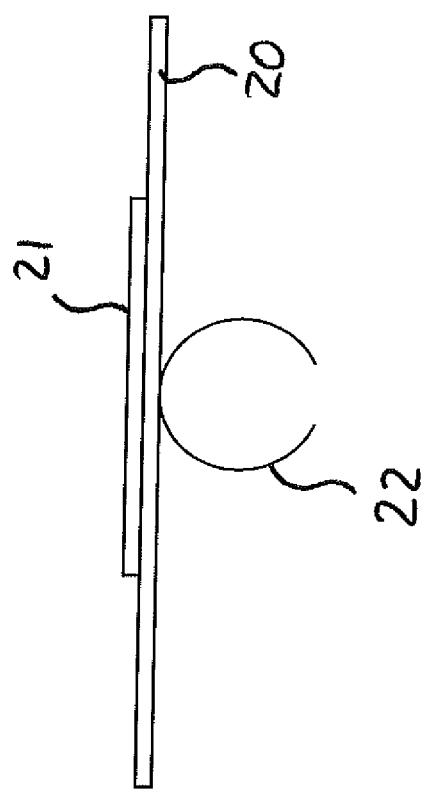

The invention is explained in greater detail below on the basis of exemplary embodiments with reference to the figures in the drawings in which:

FIG. 1 shows a schematic diagram to illustrate the use of identifiers in conjunction with an indwelling catheter and FIG. 2 shows a schematic diagram of a detachable carrier device for an identifier on an indwelling catheter.

FIG. 1 shows a schematic diagram to illustrate an indwelling catheter and/or a transfusion indwelling catheter system. With an indwelling catheter 1 a puncture cannula 2 is arranged to pass through an indwelling cannula 4 in a housing 3 so that a tip 5 of the puncture cannula 2 protrudes out of the indwelling cannula 4. When the indwelling catheter 1 is positioned, the patient's skin is punctured by the tip 5 of the puncture cannula 2. If the tip 5 of the puncture cannula 2 reaches a blood vessel, in particular a vein, blood may enter a reservoir 6 which is arranged on the housing 3 of the indwelling catheter 1 through the puncture cannula 2. The reservoir 6 is attached to the housing 3 of the indwelling catheter with the help of a flexible fastening 7, for example a plastic strip.

According to FIG. 1 the housing 3 of the indwelling catheter 1 is provided with housing identifiers 8 and the reservoir 6 is provided with reservoir identifiers 9. The codes given with the two identifiers 8, 9 are assigned to one another.

Immediately after filling or at a later point in time, the reservoir 6 according to FIG. 1 may be separated from the indwelling catheter 1 including the reservoir identifier 9 and sent for a blood test on the blood thereby sampled. The reservoir identifiers 9 may then also be duplicated so that new identifiers 10 are produced which can then be glued onto a bag 11 containing a transfusion fluid. If the transfusion fluid from the transfusion bag 11 is then to be injected into the patient on whom the indwelling catheter 1 has been placed, the person charged to do so then checks by evaluating the housing identifiers 8 as well as the new identifiers 10 on whether the transfusion fluid is suitable and admissible.

The creation of the novel identifiers 10 may be implemented by having the reservoir identifiers 9 read by means of an optical scanner for example and then the novel identifiers 10 being printed, which is possible in conjunction with a code in the form of a barcode or an alphanumeric character string, for example. If identifiers in the form of an electronic storage medium are used, a novel storage medium is written accordingly with information data making it possible in evaluation later to make the assignment to the patient having the indwelling catheter. In this way the action chain from placement of the indwelling catheter 1 until administration of a transfusion is closed.

In the embodiment shown in FIG. 1, the indwelling catheter 1 is formed with a puncture cannula 2 and indwelling cannula 4. Alternatively, it is possible to provide that the indwelling catheter has only one cannula which is suitable for both placement of the catheter and for remaining in place for a subsequent transfusion.

FIG. 2 shows one possible embodiment of a fastening means for detachable attachment of an identifier on the indwelling catheter 1 in FIG. 1. An identifier 21 is applied to a carrier 20 for example by gluing. The carrier 20 may then be detachably attached to the indwelling catheter 1 with the help of the fastening means 22 which is a type of clip fastening for example.

The features of the invention disclosed in the preceding description, the claims and the drawings may be important either individually or in any combination for the implementation of the invention in its various embodiments.

What is claimed is:

1. A method for testing a transfusion system, wherein the method comprises the following steps:
provling an indwelling catheter, comprising a cannula device, a housing for the cannula device, and a reservoir, wherein the housing has housing identifiers thereon and the reservoir has reservoir identifiers thereon, and the housing identifiers and the reservoir identifiers show mutually assigned codes;
filling the reservoir through the cannula device with blood from a source of blood;
removing the reservoir with blood from the indwelling catheter;
evaluating the reservoir identifiers;
generating fluid identifiers with a fluid code derived from the evaluation of the reservoir identifiers;
providing a transfusion fluid in a fluid reservoir, for further testing of the fluid in the fluid reservoir, and providing the fluid identifiers on the fluid reservoir;
evaluating a code given by the housing identifiers and the fluid code given by the fluid identifiers by means of an evaluation unit configured to detect and compare the two codes; and
outputting a signal by means of the evaluation unit as a function of whether or not the identifiers are recognized as assigned to one another in the comparison,
wherein, before the step of providing the transfusion fluid in the fluid reservoir is performed, the steps of generating the fluid identifiers provided to the fluid reservoir and providing the fluid identifiers on the fluid reservoir are performed.

2. The method according to claim 1, further comprising a step of supplying transfusion fluid from the fluid reservoir to the reservoir via a cannula from the fluid reservoir to the reservoir.

* * * * *